(12) United States Patent
Maytal et al.

(10) Patent No.: US 9,852,634 B2
(45) Date of Patent: Dec. 26, 2017

(54) OPERATOR ALERTNESS MONITOR

(71) Applicant: Empire Technology Development LLC, Wilmington (DE)

(72) Inventors: Benjamin Maytal, Zion (IL); Noam Maytal, Herzlia (IL)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 432 days.

(21) Appl. No.: 14/372,104

(22) PCT Filed: Oct. 25, 2013

(86) PCT No.: PCT/US2013/066910
§ 371 (c)(1),
(2) Date: Jul. 14, 2014

(87) PCT Pub. No.: WO2015/060874
PCT Pub. Date: Apr. 30, 2015

(65) Prior Publication Data
US 2016/0275798 A1 Sep. 22, 2016

(51) Int. Cl.
| G08B 13/14 | (2006.01) |
| G08G 1/16 | (2006.01) |
| G08B 21/06 | (2006.01) |
| A61B 5/18 | (2006.01) |
| B60Q 9/00 | (2006.01) |

(Continued)

(52) U.S. Cl.
CPC .............. G08G 1/166 (2013.01); A61B 5/18 (2013.01); B60Q 9/008 (2013.01); B60W 40/09 (2013.01); G08B 21/06 (2013.01); G08B 21/182 (2013.01); G08B 21/187 (2013.01); G08B 29/02 (2013.01); B60W 2040/0872 (2013.01)

(58) Field of Classification Search
CPC ...... G08B 21/06; B60K 28/066; B60K 28/06; A61B 5/01; A61B 3/113
USPC ............. 340/575, 435, 438, 449, 905, 568.1
See application file for complete search history.

(56) References Cited

U.S. PATENT DOCUMENTS 5,689,241 A * 11/1997 Clarke, Sr. ............. G08B 21/06
340/575
6,822,573 B2 * 11/2004 Basir ...................... G08B 21/06
280/735

(Continued)

FOREIGN PATENT DOCUMENTS

| KR | 20070075425 A | 7/2007 |
| KR | 1020070075425 A | 7/2007 |

OTHER PUBLICATIONS

International Search Report for International Application No. PCT/US13/66910, dated Feb. 10, 2014.

(Continued)

*Primary Examiner* — Hoi Lau
(74) *Attorney, Agent, or Firm* — Brundidge & Stanger, P.C.

(57) ABSTRACT

In one example embodiment, an operator alertness monitoring system may include a proximate condition monitor that is configured to issue an alert to direct an operator's attention to a detected hazardous condition, and an operator alertness monitor that is configured to detect the operator's physical reaction to the issued alert and instruct the proximate condition monitor to respond to the operator's detected physical reaction to the issued alert.

27 Claims, 4 Drawing Sheets

(51) Int. Cl.
  *B60W 40/09* (2012.01)
  *G08B 21/18* (2006.01)
  *G08B 29/02* (2006.01)
  *B60W 40/08* (2012.01)

(56) References Cited

U.S. PATENT DOCUMENTS

| | | | |
|---|---|---|---|
| 8,344,894 B2* | 1/2013 | Szczerba | B60K 28/066 340/435 |
| 2003/0181822 A1* | 9/2003 | Victor | A61B 3/113 600/558 |
| 2007/0164853 A1* | 7/2007 | Matsuda | B60T 8/1725 340/438 |
| 2008/0180235 A1* | 7/2008 | Chang | A61B 5/01 340/449 |
| 2012/0212353 A1* | 8/2012 | Fung | B60K 28/06 340/905 |

OTHER PUBLICATIONS

Dvijesh, S., "Contact-free Stress Monitoring for User's Divided Attention," Human-Computer Interaction, pp. 127-134 (2008).

Or, C.K.L., and Duffy, V.G., "Development of a facial skin temperature-based methodology for non-intrusive mental workload measurement ," Occupational Ergonomics, vol. 7, No. 2, pp. 83-94 (2007).

Tsiamyrtzis P., et al., "Imaging Facial Physiology for the Detection of Deceit," International Journal of Computer Vision February, vol. 71, Issue 2, pp. 197-214 (2007).

* cited by examiner

OPERATOR ALERTNESS MONITOR

CROSS-REFERENCE TO RELATED APPLICATION

This Application is the U.S. National Stage filing under 35 U.S.C. §371 of International Application No. PCT/US13/66910 filed on Oct. 25, 2013. The disclosures of both applications are hereby incorporated herein by reference in their entireties.

TECHNICAL FIELD

The embodiments described herein pertain generally to providing a high level of alertness for an operator of a monitored system.

BACKGROUND

Unless otherwise indicated herein, the approaches described in this section are not prior art to the claims in this application and are not admitted to be prior art by inclusion in this section.

Automated controls continue to be integrated into systems that have traditionally been entrusted to human operator controls. For example, long distance flights are being entrusted to auto-pilots on an increasing scale; operation of building maintenance systems, e.g., climate control, is being entrusted more to automated control systems; and even the task of parallel parking of some current high-end automobile models is being surrendered to an automated system.

SUMMARY

In one example embodiment, an operator alertness monitoring system includes a proximate condition monitor that is configured to issue an alert to direct an operator's attention to a detected hazardous condition, and an operator alertness monitor that is configured to detect the operator's physical reaction to the issued alert and instruct the proximate condition monitor to respond to the operator's detected physical reaction to the issued alert.

In another example embodiment, a method to provide driver safety, under control of a processor-enabled monitoring system, includes a processor positioning a thermal-sensing device to monitor a driver's body temperature, monitoring driving conditions, issuing an alert in response to determining that the monitored driving conditions include a predefined hazard, detecting an increase in a driver's body temperature within a predetermined amount of time after the alert has been issued, and issuing a reinforced alert.

In yet another example embodiment, a non-transitory computer-readable medium may store executable-instructions that, when executed, cause one or more processors to perform operations including: monitoring real-time physiological data for the operator, relative to pre-stored physiological data for the operator; monitoring operating conditions; detecting an above-threshold increase in the monitored real-time physiological data for the operator within passage of a predetermined amount of time when the monitored operating conditions indicate an operating hazard; and amplifying an existing alert to the operator.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

Figure 1:
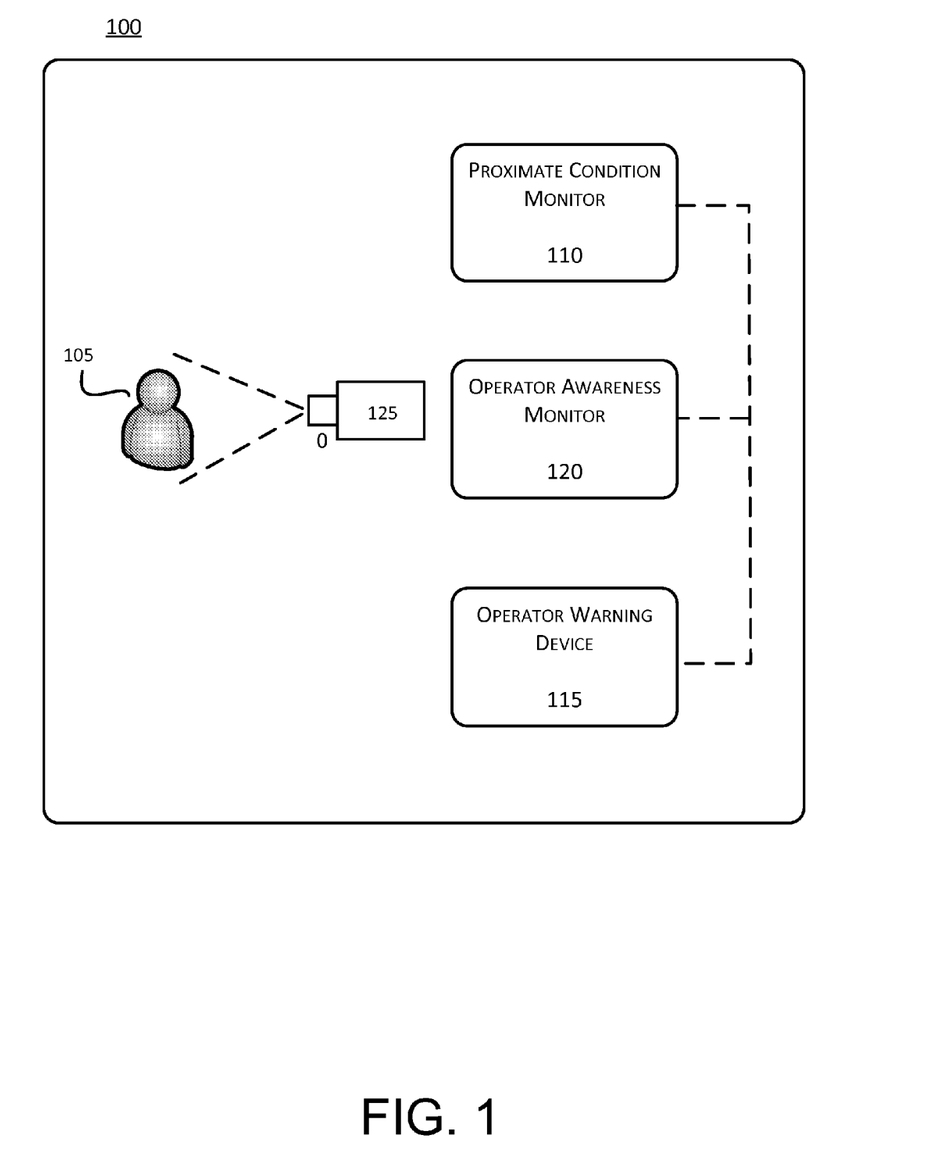
FIG. 1 shows an example configuration of a system in which an operator alertness monitor may be implemented, arranged in accordance with at least some embodiments described herein.

FIG. 1 shows an example configuration of a system 100 in which an operator alertness monitor may be implemented, arranged in accordance with at least some embodiments described herein. As depicted, a user 105 may be a subject of system 100 that includes, at least, a proximate condition monitor 110, an operator warning device 115, an operator alertness monitor 120, and a biometric sensor 125. Proximate condition monitor 110, operator warning device 115, operator alertness monitor 120, and biometric sensor 125 may, respectively, be implemented as a hardware device, as software, as firmware, or any combination thereof. Additionally, various implementations for monitoring operator alertness may contemplate any one or more of proximate condition monitor 110, operator alertness monitor 120, biometric sensor 125, operator warning device 115, or even user 105 being disposed external to system 100, without departing from the scope of the embodiments described herein.

System 100 may refer to, as non-limiting examples, a vehicle, a structure, an airplane, a datacenter, etc., in part or in its entirety, that may implement user operation and/or control even on a limited basis. Thus, system 100 may include automated components that may operate free of user intervention or involvement, at least on a limited basis. Non-limiting examples of such automated components may include auto-steering, or components configured to monitor an environment surrounding system 100 or monitor operational performance of sub-systems. In an automobile or a vehicle, non-limiting examples of such sub-systems may include engines, brakes, climate control, parking assistance, lane departure, blind-spot monitoring, etc. In a building or structure, non-limiting examples of such sub-systems may include climate control, building security, fire alarm, etc. In an airplane, non-limiting examples of such sub-systems may include auto-pilot, engines, brakes, landing gear, air pressure, climate control, etc. In a datacenter, non-limiting examples of such sub-systems may include climate control, device temperature sensor, etc. Accordingly, the aforementioned operation and/or control may include trouble-shooting or safety monitoring.

A non-limiting example of system 100 may include, in part or in whole, an operator alertness monitoring system that includes a proximate condition monitor that is configured to issue an alert to direct an operator's attention to a detected hazardous condition, and an operator alertness monitor that is configured to detect the operator's physiological reaction to the issued alert and instruct the proximate condition monitor to respond to the operator's detected physiological reaction to the issued alert.

User 105 may refer to a person who exercises any level of operational control, trouble-shooting responsibilities, and/or safety monitoring over one or more of the aforementioned automated components of system 100.

Proximate condition monitor 110 may refer to a component or module that may be configured, designed, and/or programmed to monitor a surrounding environment of system 100. For example, if system 100 is implemented as an automobile or vehicle, proximate condition monitor 110 may be configured, designed, and/or programmed to detect the presence of driving obstacles or driving hazards that may come within a threshold distance of system 100. The threshold distance may be a static distance, e.g., three (3) feet, a set of tiered distances that invoke different levels of warnings, or a set of dynamically determined distances that are based on a velocity and acceleration of the automobile or vehicle. Non-limiting examples of proximate condition monitor 110 may include a motion sensor, digital video recorder, sonar device, etc.

Alternative embodiments of proximate condition monitor 110 may be implemented, respectively, to monitor and detect existing or potentially dangerous or hazardous conditions relative to system 100; to monitor external environmental conditions, e.g., precipitation, road conditions, winds, extreme temperatures, etc.; to monitor various internal operational components (e.g., mechanical, hardware, and software) relative to system 100; and/or to monitor other conditions that may otherwise affect the performance of system 100 and/or the safety of user 105 or any other person in or near system 100 during operation thereof.

Operator warning device 115 may refer to a device that may be configured, designed, and/or programmed to provide a visual and/or audio warning or stimulus subsequent to proximate condition monitor 110 determining the existence of one or more conditions that may affect the performance of system 100 and/or the safety of user 105 or any other person in or near system 100 during operation thereof.

Non-limiting examples of such visual and/or audio warning produced by operator warning device 115 may include one or more of: an illuminated icon, e.g., battery, on a dashboard of an automobile or vehicle; a textual display, e.g., "close object," on a dashboard or head-up display of an automobile or vehicle; a prerecorded audio warning to advise of a potential or existing dangerous or hazardous condition relative to system 100; internal lights of system 100 being turned on.

Operator alertness monitor 120 may refer to a component or module that may be configured, designed, and/or programmed to monitor one or more physiological responses by user 105 in response to the visual and/or audio warning or stimulus subsequent to proximate condition monitor 110 determining the existence of a potential or existing dangerous or hazardous condition relative to system 100. That is, operator alertness monitor 120 may be configured, designed, and/or programmed to monitor one or more physiological responses by user 105 within a predetermined amount of time after one or more visual and/or audio warnings has been produced by operator warning device 150. Non-limiting example embodiments of operator alertness monitor 120 may include a database to store a pre-recorded physiological profile of user 105 including, but not limited to, a resting heart rate, a resting body temperature, etc.; and/or standardized or threshold values thereof. Alternatively, or in addition, operator alertness monitor 120 may be configured to receive a storage device, e.g., a flash drive, on which the aforementioned physiological profile for user 105 may be stored, for utilization in providing operator alertness. Alternatively, or in addition, operator alertness monitor 120 may further be wirelessly connected to a service provider, e.g., OnStar®, to which user 105 and/or system 100 may be registered, at which the aforementioned physiological profile for user 105 may be stored.

Biometric sensor 125 may refer to a device that may be configured, designed, and/or programmed to measure physiological responses for user 105 at any given time. Non-limiting examples of the physiological responses measured by biometric sensor 125 may include: a thermal imaging camera configured to monitor and measure the skin temperature for user 105, e.g., facial temperature; a thermal monitor that may be embedded in, e.g., a seat, steering wheel, etc., of system 100, and configured to monitor and measure the body temperature for user 105; a pulse monitor that may be embedded in, e.g., a seat, steering wheel, etc., of system 100, and configured to monitor and measure the pulse rate for user 105; etc. In accordance with various example embodiments, biometric sensor 125 may be positioned to obtain virtually instantaneous readings of physiological parameters for user 105 at a given moment. Thus, for example, as a thermal imaging camera, biometric sensor 125 may be automatically or manually positioned to focus on a designated portion of the anatomy, e.g., the face, of user 105 during a beginning stage of use.

In non-limiting example embodiments, biometric sensor 125 may be positioned or physically integrated with operator alertness monitor 120, connected to operator alertness monitor 120 via a wired connection, or connected to operator alertness monitor 120 via a wired connection such as a short-range communication protocol.

Further, depending upon an implementation of system 100, which may include, as non-limiting examples, a vehicle, structure, airplane, datacenter, etc., in part or in its entirety, biometric sensor 125 may be disposed and positioned appropriate in an operator's control panel, control console, cockpit, etc.

Accordingly, operator alertness monitor 120, in combination with biometric sensor 125, may operate to continuously or periodically monitor one or more physiological responses of user 105 within a predetermined amount of time after one or more visual and/or audio warnings has been produced by operator warning device 115. By way of example, subsequent to a visual and/or audio warning being produced by operator warning device 115, if the body/skin temperature and/or pulse rate of user 105 is measured or detected as increasing by a predetermined amount within a threshold amount of time, operator alertness monitor 120 may determine that user 105 is indeed sufficiently aware of the detected potential or existing dangerous or hazardous condition relative to system 100 in order to take corrective action. The determination may be predicated upon an assumption that an operator who is made aware of a potentially dangerous or hazardous condition may incur a surge of adrenaline that results in a discernible increase in body/skin temperature and/or pulse rate.

However, if the body/skin temperature and/or pulse rate of user 105 is measured or detected as remaining beneath the aforementioned predetermined amount thereof, operator alertness monitor 120 may operatively prompt operator warning device 115 to produce a heightened visual and/or audio warning or stimulus to alert user 105 of the existing or potential dangerous or hazardous condition relative to system 100. Non-limiting examples of the heightened warning or stimulus may include a brighter version of the previously produced visual warning and/or a louder version of the previously produced audio warning. Alternatively, or in addition, operator warning device may be further configured, designed, and/or programmed to implement corrective action such as reducing a current velocity of system 100, taking evasive action, turning system 100 away from a detected obstacle, shutting system 100 down in part or in whole, etc. Of course, such corrective action is largely dependent upon an implementation of system 100, e.g., as a vehicle, structure, airplane, datacenter, etc.

Figure 2:
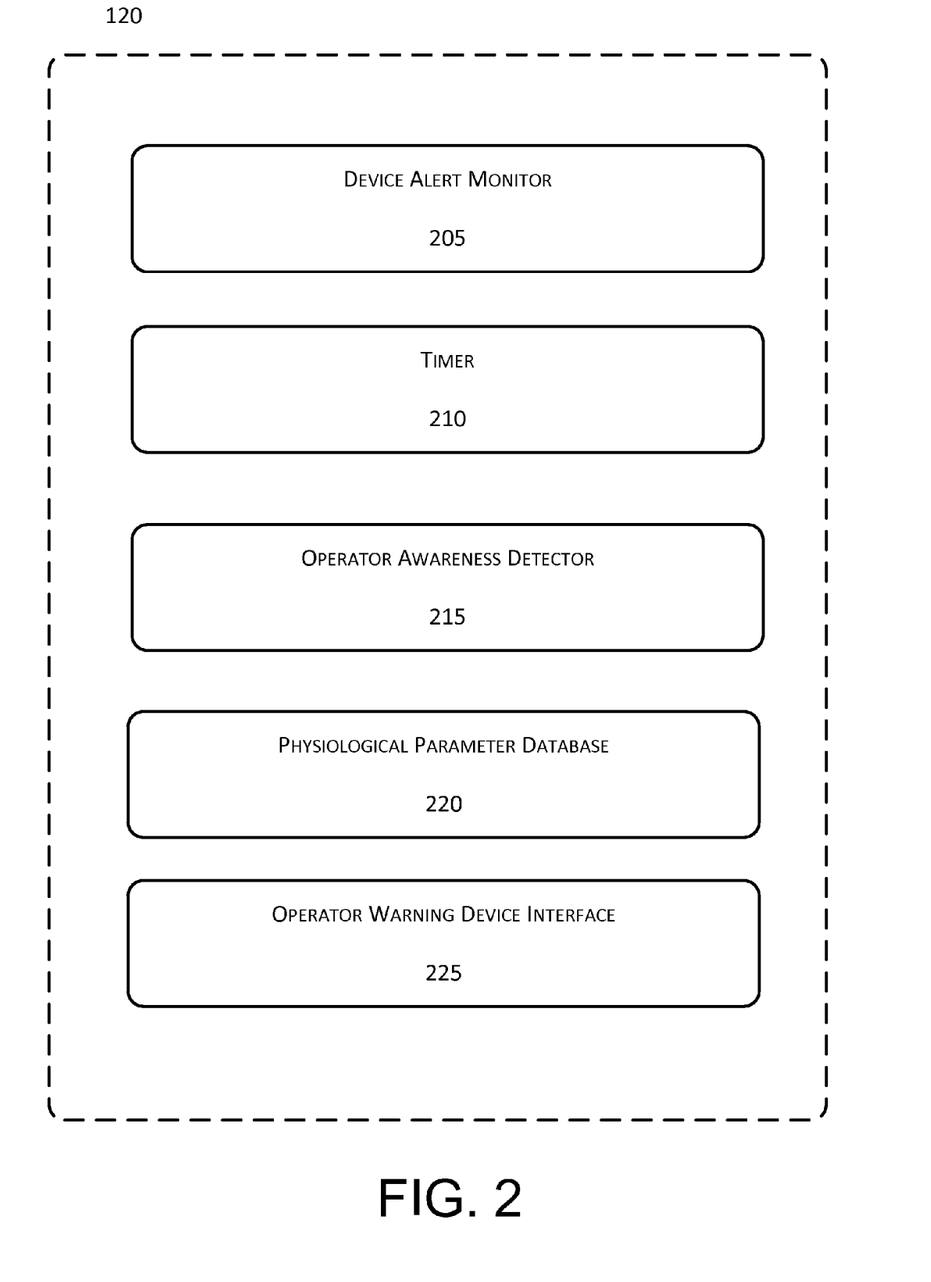
FIG. 2 shows an example configuration of an operator alertness monitor, arranged in accordance with at least some embodiments described herein.

FIG. 2 shows an example configuration of operator alertness monitor 120, arranged in accordance with at least some embodiments described herein. As depicted, operator alertness monitor 120 may include, at least, a device alert monitor 205, a timer 210, an operator awareness detector 215, a physiological parameter database 220, and an operator warning device interface 230. Device alert monitor 205, timer 210, operator awareness detector 215, physiological parameter database 220, and operator warning device interface 225 may, respectively, be implemented as a hardware device, as software, as firmware, or any combination thereof. Additionally, various implementations for monitoring operator alertness may contemplate physiological parameter database 220 being disposed external to operator alertness monitor 120 or even system 100, without departing from the scope of the embodiments described herein.

Device alert monitor 205 may refer to a component or module that may be configured, designed, and/or programmed to monitor and detect whether operator warning device 115 has produced a visual and/or audio warning or stimulus subsequent to proximate condition monitor 110 determining the existence of one or more conditions that may affect the performance of system 100 and/or the safety of user 105 or any other person in or near system 100 during operation thereof. Alternatively, or in addition, device alert monitor 205 may be configured, designed, and/or programmed to monitor proximate condition monitor 110 to detect whether proximate condition monitor 110 has determined the existence of one or more such existing or potential dangerous or hazardous conditions, relative to system 100.

Timer 210 may refer to a timer that may be communicatively coupled to device alert monitor 205 further configured and/or programmed to commence marking time at a substantially same instant that device alert monitor 205 has detected operator warning device 115 producing a visual and/or audio warning or stimulus subsequent to proximate condition monitor 110 determining the existence of one or more conditions that may affect the performance of system 100 and/or the safety of user 105 or any other person in or near system 100 during operation thereof. Alternatively, or in addition, timer 210 may be communicatively coupled to proximate condition monitor 110 and/or operator warning device 115 to commence marking time at a substantially same instant that an existing or potential dangerous or hazardous condition has been detected relative to system 100.

Operator awareness detector 215 may refer to a component or module that is communicatively coupled to biometric sensor 125 and further configured, designed, and/or programmed to monitor physiological parameters, including but not limited to body/skin temperature and/or pulse rate, for user 105. Thus, when device alert monitor 205 has detected that operator warning device 115 has produced a visual and/or audio warning or stimulus subsequent to proximate condition monitor 110 determining an existing or potential dangerous or hazardous condition relative to system 100, operator awareness detector 215 may further measure any increase in the physiological parameters measured by biometric sensor 125. Operator awareness detector 215 may compare any measured increase in the measured physiological parameters to a predetermined threshold, e.g., 2° F., 10 beats/minute, that have been pre-established as being indicative of a physiological response to an external stimulus or emergency, such as a surge of adrenaline that results in a discernible increase in body/skin temperature and/or pulse rate. Accordingly, within a predetermined amount of time, as monitored by timer 210, operator awareness detector 215 may determine whether or not user 105 has heeded a visual and/or audio warning produced by operator warning device 115 and is aware of the existing or potential dangerous or hazardous condition relative to system 100.

Operator awareness detector 215 may be further configured, designed, and/or programmed to record the aforementioned physiological parameters for user 105 within a predetermined amount of time, as marked by timer 210. The predetermined amount of time may vary in accordance with the detected existing or potential dangerous or hazardous condition relative to system 100. As non-limiting examples, if an oncoming vehicle is detected, the predetermined amount of time may be less than one second; if rumble strips beneath a corresponding vehicle's wheels are detected, the predetermined amount may be three (3) seconds or less; or if an overheating engine is detected, the predetermined amount of time may be 15 seconds or less. The preceding values are provided as examples only to demonstrate the non-uniformity and dynamic nature of the aforementioned predetermined amount of time, and are not intended to be limiting to any of the example embodiments described herein.

Physiological parameter database 220 may refer to a local database or communicative connection thereto or a receptacle for an external device in which may be stored at least a pre-recorded physiological profile for user 105.

In accordance with the various embodiments described above, operator awareness detector 215 may compare any measured increase in the measured physiological parameters of user 105 to a pre-recorded physiological profile of user 105 including, but not limited to, a resting heart rate, a resting body temperature, etc.; and/or standardized or threshold values thereof. Such pre-recorded physiological profile and/or standardized or threshold values may be stored, alternatively or in addition, on an external device, e.g., flash drive, received by operator alertness monitor 120; or hosted by a remote server or third-party service provider, e.g., OnStar®, to which user 105 and/or system 100 may be registered.

Operator warning device interface 225 may refer to a component or module that is communicatively coupled to operator warning device 115 and further configured, designed, and/or programmed to transmit an indication of the physiological parameters for user 105, as monitored and measured within a predetermined amount of time corresponding to the detected existing or potential dangerous or hazardous condition relative to system 100, as marked by timer 210. Thus, if the physiological parameters for user 105 monitored and measured within the predetermined amount of time indicate that user 105 is sufficiently aware of the detected existing or potential dangerous or hazardous condition relative to system 100 in order to take corrective action, then operator warning device interface 225 may transmit an instruction for operator warning device 115 to turn off an activated visual and/or audio warning.

Further, if the physiological parameters for user 105 monitored and measured within the predetermined amount of time indicate that user 105 is not sufficiently aware of the detected existing or potential dangerous or hazardous condition relative to system 100 in order to take corrective action, then operator warning device interface 225 may transmit an instruction for operator warning device 115 to produce a heightened visual and/or audio warning or stimulus to alert user 105 of the existing or potential dangerous or hazardous condition relative to system 100. As described above, non-limiting examples of the heightened warning or stimulus may include a brighter version of the previously produced visual warning and/or a louder version of the previously produced audio warning. Alternatively, or in addition, operator warning device interface 225 may transmit an instruction for operator warning device to activate a corrective action such as reducing a current velocity of system 100, taking evasive action, turning system 100 away from a detected obstacle, shutting system 100 down in part or in whole, etc. Of course, such corrective action is largely dependent upon an implementation of system 100, e.g., as a vehicle, structure, airplane, datacenter, etc. In accordance with further alternative embodiments, operator warning device 115 may already be programmed to activate one or more corrective actions, without instruction or prompting from operator warning device interface 225.

Figure 3:
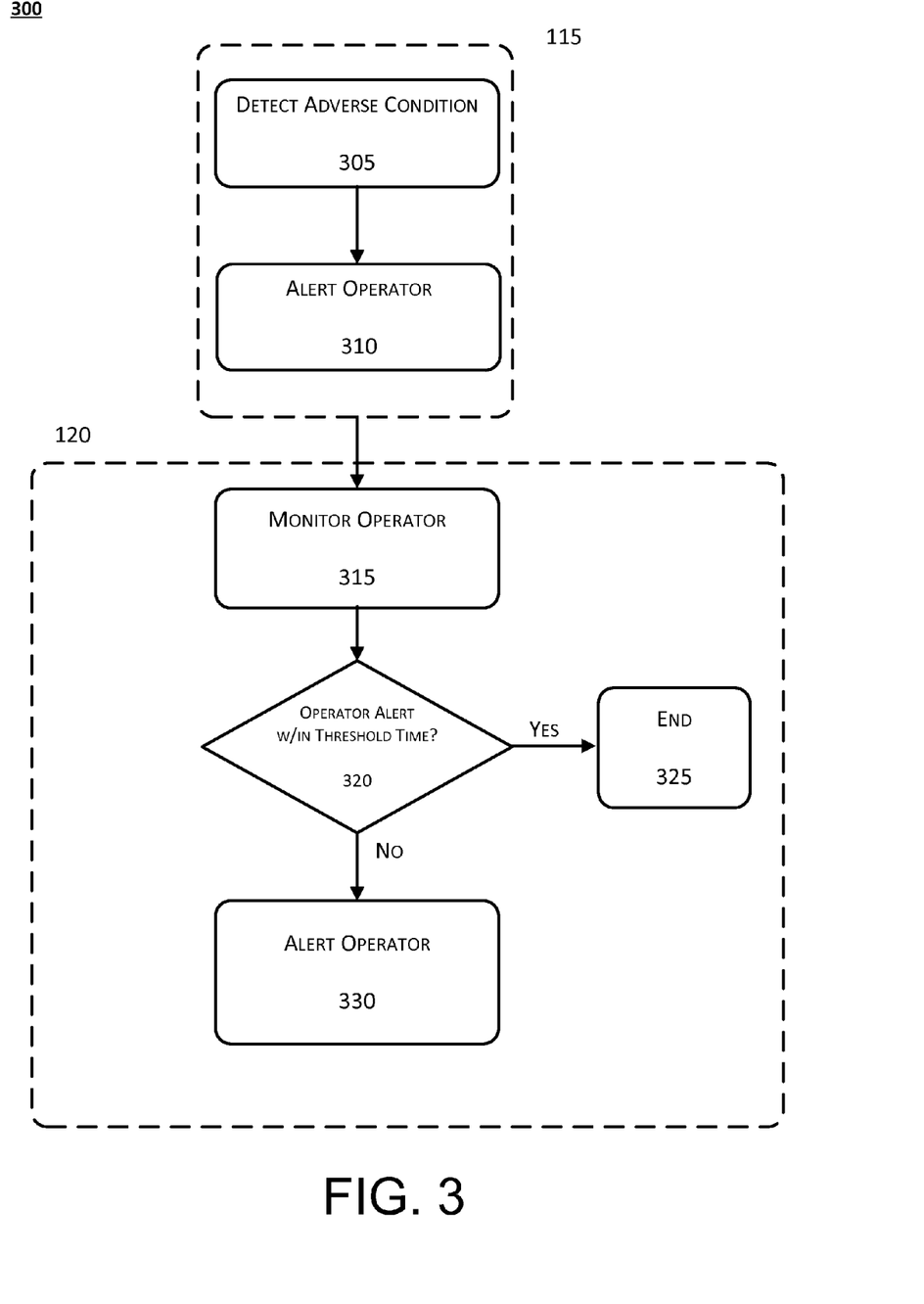
FIG. 3 shows an example processing flow of operations executed by an operator alertness monitor, arranged in accordance with at least some embodiments described herein.

FIG. 3 shows an example processing flow 300 of operations executed by an operator alertness monitor, arranged in accordance with at least some embodiments described herein. Processing flow 300 may be implemented by the depicted embodiment of datacenter system configuration 100 or various permutations thereof. Processing flow 300 may include one or more operations, actions, or functions depicted by one or more blocks 305, 310, 315, 320, 325, and 330. Although illustrated as discrete blocks, various blocks may be divided into additional blocks, combined into fewer blocks, or eliminated, depending on the desired implementation. Further, blocks 305 and 310 are depicted as being attributed to operator warning device 115 and blocks 315, 320, 325, and 330 are depicted as being attributed to operator awareness monitor 120. Such depiction is consistent with some of the example embodiments described with regard to FIGS. 1 and 2. However, alternatively, embodiments described herein may contemplate respective blocks of processing flow 300 being attributed to different features of system 100. Processing may begin at block 305.

Block 305 (Detect Adverse Condition) may refer to proximate condition monitor 110 detecting one or more existing or potential dangerous or hazardous conditions that may affect the performance of system 100 and/or the safety of user 105 or any other person in or near system 100 during operation thereof.

Block 310 (Alert Operator) may refer to operator warning device 115 providing or activating a visual and/or audio warning or stimulus subsequent to proximate condition monitor 110 detecting the one or more existing or potential dangerous or hazardous conditions relative to system 100. Non-limiting examples of such visual and/or audio warning produced by operator warning device 115 may include one or more of: an illuminated icon, e.g., battery, on a dashboard of an automobile or vehicle; a textual display, e.g., "close object," on a dashboard or head-up display of an automobile or vehicle; a prerecorded audio warning to advise of a potential or existing dangerous or hazardous condition relative to system 100; internal lights of system 100 being turned on. Block 310 may be followed by decision block 315.

Block 315 (Monitor Operator) may refer to biometric sensor 125 and operator awareness detector 215, serially or in combination, measuring and monitoring physiological parameters for user 105 upon activation of timer 210, which may occur at the time operator warning device provides or activates a visual and/or warning or stimulus or, alternatively, at the time proximate condition monitor 110 detects one or more existing or potential dangerous or hazardous conditions relative to system 100. Block 315 may be followed by decision block 320.

Decision block 320 (Operator Alert Within Threshold Time?) may refer to operator awareness detector 215 determining whether biometric sensor 125 and operator awareness detector 215, serially or in combination, have detected a sufficient increase in one or more of the monitored and measured physiological parameters for user 105 within the predetermined amount of time corresponding to the detected adverse condition. That is, decision block 320 may refer to operator awareness detector 215 determining whether or not user 105 has heeded a visual and/or audio warning produced by operator warning device 115 and is aware of the existing or potential dangerous or hazardous condition relative to system 100. Upon a positive determination, decision block 320 may be followed by block 325; but upon a negative determination, decision block 320 may be followed by block 330.

Block 325 (End) may refer to operator warning device interface 225 transmitting an instruction for operator warning device 115 to turn off an activated visual and/or audio warning when the physiological parameters for user 105 monitored and measured within the predetermined amount of time indicate that user 105 is sufficiently aware of the detected existing or potential dangerous or hazardous condition relative to system 100 in order to take corrective action.

Block 330 (Alert Operator) may refer to operator warning device interface 225 transmitting an instruction for operator warning device 115 to produce a heightened visual and/or audio warning or stimulus to alert user 105 of the existing or potential dangerous or hazardous condition relative to system 100.

Accordingly, processing flow 300, as implemented by various modules or components of system 100, may provide an increased level of operator alertness.

Figure 4:
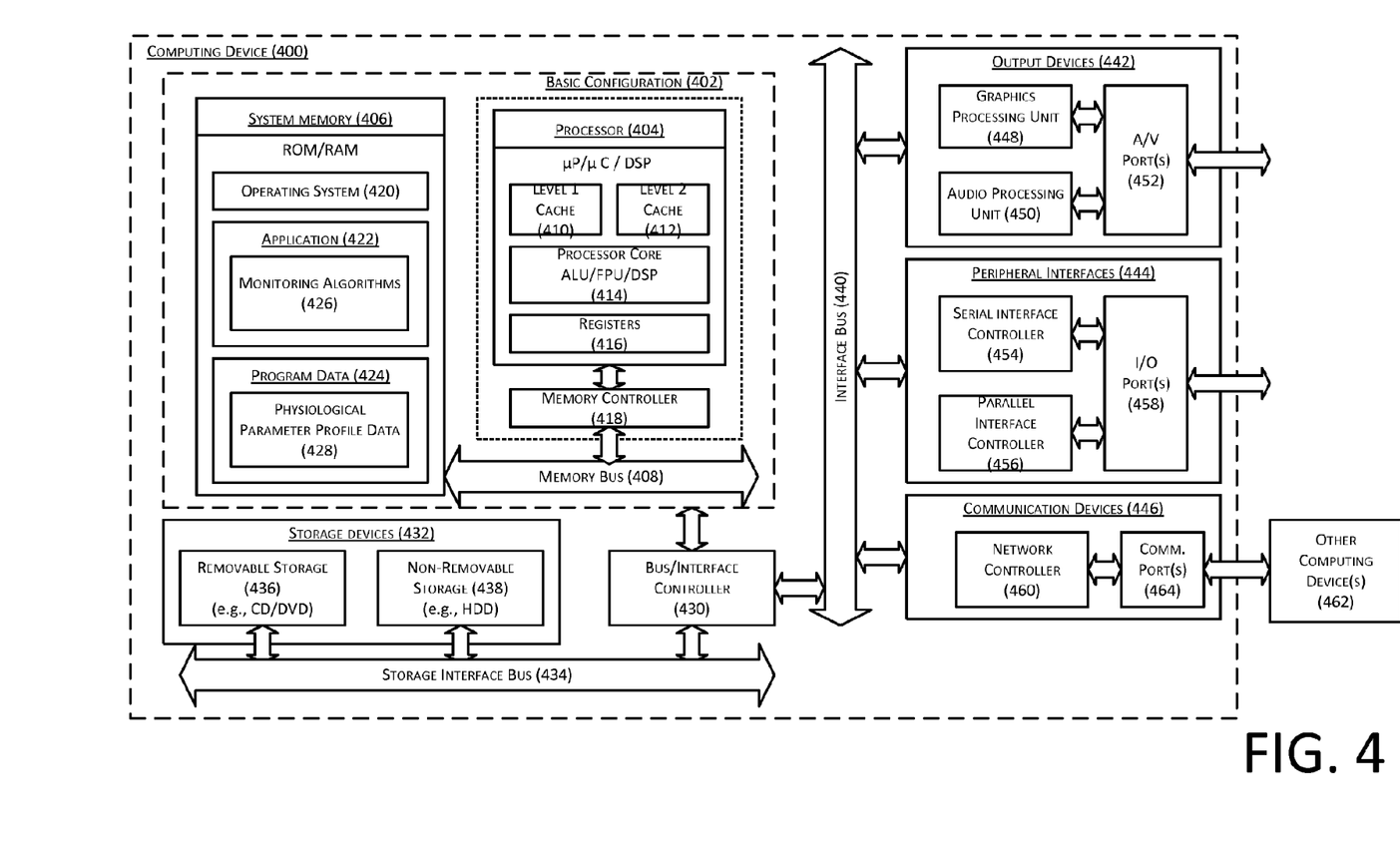
FIG. 4 shows a block diagram illustrating an example computing device by which various example solutions described herein may be implemented, arranged in accordance with at least some embodiments described herein.

FIG. 4 shows a block diagram illustrating an example computing device by which various example solutions described herein may be implemented, arranged in accordance with at least some embodiments described herein.

In a very basic configuration 402, computing device 400 typically includes one or more processors 404 and a system memory 406. A memory bus 408 may be used for communicating between processor 404 and system memory 406.

Depending on the desired configuration, processor 404 may be of any type including but not limited to a microprocessor (µP), a microcontroller (µC), a digital signal processor (DSP), or any combination thereof. Processor 404 may include one or more levels of caching, such as a level one cache 410 and a level two cache 412, a processor core 414, and registers 416. An example processor core 414 may include an arithmetic logic unit (ALU), a floating point unit (FPU), a digital signal processing core (DSP Core), or any combination thereof. An example memory controller 418 may also be used with processor 404, or in some implementations, memory controller 418 may be an internal part of processor 404.

Depending on the desired configuration, system memory 406 may be of any type including but not limited to volatile memory (such as RAM), non-volatile memory (such as ROM, flash memory, etc.) or any combination thereof. System memory 406 may include an operating system 420, one or more applications 422, and program data 424. Application 422 may include one or more monitoring algorithms 426 that may be arranged to perform the functions as described herein including those described with respect to processing flow 300 of FIG. 3. Program data 424 may include physiological parameter profile data 428 that may be utilized for the comparisons performed by the various monitoring algorithms 426 as described herein. Physiological parameter profile data 428 may include profile data for user 105 or for an anticipated generic or default user of system 100. In some embodiments, application 422 may be arranged to operate with program data 424 on operating system 420 such that implementations of monitoring operator alertness may be provided as described herein. This described basic configuration 402 is illustrated in FIG. 4 by those components within the inner dashed line.

Computing device 400 may have additional features or functionality, and additional interfaces to facilitate communications between basic configuration 402 and any required devices and interfaces. For example, a bus/interface controller 430 may be used to facilitate communications between basic configuration 402 and one or more data storage devices 432 via a storage interface bus 434. Data storage devices 432 may be removable storage devices 436, non-removable storage devices 438, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 406, removable storage devices 436 and non-removable storage devices 438 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 400. Any such computer storage media may be part of computing device 400.

Computing device 400 may also include an interface bus 440 for facilitating communication from various interface devices (e.g., output devices 442, peripheral interfaces 444, and communication devices 446) to basic configuration 402 via bus/interface controller 430. Example output devices 442 include a graphics processing unit 448 and an audio processing unit 450, which may be configured to communicate to various external devices such as a display or speakers via one or more A/V ports 452. Example peripheral interfaces 544 include a serial interface controller 454 or a parallel interface controller 456, which may be configured to communicate with external devices such as input devices (e.g., keyboard, mouse, pen, voice input device, touch input device, etc.) or other peripheral devices (e.g., printer, scanner, etc.) via one or more I/O ports 458. An example communication device 446 includes a network controller 460, which may be arranged to facilitate communications with one or more other computing devices 462 over a network communication link via one or more communication ports 464.

The network communication link may be one example of a communication media. Communication media may typically be embodied by computer readable instructions, data structures, program modules, or other data in a modulated data signal, such as a carrier wave or other transport mechanism, and may include any information delivery media. A modulated data signal may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 400 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 400 may also be implemented as a server or a personal computer including both laptop computer and non-laptop computer configurations.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein may be implemented, e.g., hardware, software, and/or firmware, and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation;

or, yet again alternatively, the implementer may opt for some combination of hardware, software, and/or firmware.

The foregoing detailed description has set forth various embodiments of the devices and/or processes for system configuration 100 via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers, e.g., as one or more programs running on one or more computer systems, as one or more programs running on one or more processors, e.g., as one or more programs running on one or more microprocessors, as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a compact disk (CD), a digital versatile disk (DVD), a digital tape, a computer memory, etc.; and a transmission type medium such as a digital and/or an analog communication medium, e.g., a fiber optic cable, a waveguide, a wired communication link, a wireless communication link, etc.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors, e.g., feedback for sensing position and/or velocity; control motors for moving and/or adjusting components and/or quantities. A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Lastly, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general, such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general, such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. An operator alertness monitoring system, comprising:
   a proximate condition monitor configured to:
     detect a hazardous condition, wherein the detected hazardous condition comprises one or more of an external obstacle or a localized technical failure;
     issue an alert to direct an operator's attention to the detected hazardous condition; and
   an operator alertness monitor configured to:
     detect an operator's physiological reaction to the issued alert within a predetermined time period, wherein the predetermined time period varies in accordance with a type of the detected hazardous condition, and
     instruct the proximate condition monitor to respond to the operator's physiological reaction to the issued alert.

2. The operator alertness monitoring system of claim 1, wherein the proximate condition monitor is further configured to detect the hazardous condition prior to issuance of the alert.

3. The operator alertness monitoring system of claim 1, wherein the operator alertness monitoring system is included in an automobile.

4. The operator alertness monitoring system of claim 1, wherein the hazardous condition is an approaching object.

5. The operator alertness monitoring system of claim 1, wherein the hazardous condition is a mechanical failure.

6. The operator alertness monitoring system of claim 1, wherein the proximate condition monitor is configured to issue the alert by sounding an audible alarm.

7. The operator alertness monitoring system of claim 1, wherein the proximate condition monitor is configured to issue the alert by displaying a warning message.

8. The operator alertness monitoring system of claim 1, wherein the operator alertness monitor includes a thermal imaging camera.

9. The operator alertness monitoring system of claim 1, wherein:
   the operator alertness monitoring system is included in an automobile, and
   the operator alertness monitor includes a thermal imaging camera, directed at a driver's seat.

10. The operator alertness monitoring system of claim 1, wherein the operator alertness monitor includes a thermal imaging camera that is configured to detect the operator's physiological reaction to the issued alert by detecting an increase in an operator's skin temperature, relative to a predetermined threshold value, within a predetermined amount of time after the proximate condition monitor issues the alert.

11. The operator alertness monitoring system of claim 10, wherein the predetermined threshold value includes an operator's base body temperature as preset for the operator alertness monitoring system.

12. The operator alertness monitoring system of claim 1, wherein the operator alertness monitor includes a body temperature sensor connected to a steering wheel that is configured to detect the operator's physiological reaction to the issued alert by detecting an increase in the operator's skin temperature, relative to a predetermined threshold value, within a predetermined amount of time after the proximate condition monitor issues the alert.

13. The operator alertness monitoring system of claim 1, wherein the operator alertness monitor is further configured to instruct the proximate condition monitor to respond to the operator's detected physiological reaction to the issued alert by instructing that the issued alert be amplified.

14. The operator alertness monitoring system of claim 1, wherein the operator alertness monitor is further configured to instruct the proximate condition monitor to respond to the operator's detected physiological reaction to the issued alert by instructing that the issued alert cease.

15. A method to provide driver safety, under control of a processor-enabled monitoring system, the method comprising:
   monitoring, by a thermal-sensing device communicatively coupled to the processor, a driver's body temperature;
   monitoring, by the processor, driving conditions;
   determining, by the processor, that the monitored driving conditions include a predefined hazard, wherein the predefined hazard comprises one or more of an external obstacle or a localized technical failure;
   issuing, by the processor, an alert in response to the determination that the monitored driving conditions include the predefined hazard;
   detecting, by the processor, an increase in a driver's body temperature within a predetermined amount of time after the alert is issued within a predetermined time period, wherein the predetermined time period varies in accordance with a type of the detected hazardous condition; and
   issuing, by the processor, a reinforced alert.

16. The method of claim 15, wherein the detecting includes monitoring the driver's body temperature relative to stored threshold data pertaining to the driver.

17. The method of claim 15, wherein the detecting includes monitoring the driver's body temperature relative to objective stored threshold data.

18. The method of claim 15, wherein the thermal-sensing device includes a thermal imaging camera.

19. The method of claim 15, wherein the thermal-sensing device includes a body temperature sensor embedded within a driver's seat.

20. The method of claim 15, wherein the issuing of the alert includes at least one of sounding an audible alarm or displaying a warning message.

21. The method of claim 20, wherein the issuing of the reinforced alert includes at least one of sounding a louder audible alarm or displaying a brighter warning message.

22. A non-transitory computer-readable medium storing executable instructions that, when executed, cause one or more processors to perform operator safety acts to:
  monitor real-time physiological data for the operator, relative to pre-stored physiological data for the operator;
  monitor operating conditions;
  determine that the monitored operating conditions indicate an operating hazard, wherein the operating hazard comprises one or more of an external obstacle or a localized technical failure;
  detect an above-threshold increase in the monitored real-time physiological data for the operator within passage of a predetermined amount of time responsive to the monitored operating conditions indicating the operating hazard wherein the predetermined time period varies in accordance with a type of the detected operating hazard; and
  amplify an existing alert to the operator.

23. The non-transitory computer-readable medium of claim 22, wherein the real-time physiological data for the operator includes at least one of body temperature, pulse-rate, or blood pressure.

24. The non-transitory computer-readable medium of claim 22, wherein the monitored operating conditions include external weather conditions, external road surface conditions, external objects within a predefined perimeter, internal mechanical operations, or internal electrical operations.

25. The non-transitory computer-readable medium of claim 24, wherein the operating hazard further comprises any one of precipitation, rumble strips, another vehicle within the predetermined perimeter, an engine malfunction, or a software malfunction.

26. The non-transitory computer-readable medium of claim 23, wherein the existing alert includes at least one of an audible alarm or a displayed warning message.

27. The operator alertness monitoring system of claim 1, wherein the proximate condition monitor is further configured to implement corrective action, wherein the corrective action includes one or more of reducing a current velocity of an automobile, taking evasive action, turning system away from a detected obstacle, and shutting the automobile down.

* * * * *

UNITED STATES PATENT AND TRADEMARK OFFICE
CERTIFICATE OF CORRECTION

PATENT NO. : 9,852,634 B2
APPLICATION NO. : 14/372104
DATED : December 26, 2017
INVENTOR(S) : Maytal et al.

It is certified that error appears in the above-identified patent and that said Letters Patent is hereby corrected as shown below:

On the Title Page

In Item (71), under "Applicant", in Column 1, Lines 1-2, delete "Empire Technology Development LLC, Wilmington (DE)" and insert -- Empire Technology Development LLC, Wilmington, DE (US) --, therefor.

Signed and Sealed this
First Day of May, 2018

Andrei Iancu
*Director of the United States Patent and Trademark Office*